(12) United States Patent
Schwartz et al.

(10) Patent No.: US 6,913,888 B2
(45) Date of Patent: Jul. 5, 2005

(54) TOLL-LIKE RECEPTOR 4 MUTATIONS

(75) Inventors: David Schwartz, Chapel Hill, NC (US); Eva Lorenz, Winston-Salem, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/316,191

(22) Filed: Dec. 11, 2002

(65) Prior Publication Data

US 2003/0232352 A1 Dec. 18, 2003

Related U.S. Application Data

(60) Provisional application No. 60/338,680, filed on Dec. 11, 2001.

(51) Int. Cl.$^7$ .......................... C12Q 1/68; G01N 33/53; C12P 21/06; C07K 14/00
(52) U.S. Cl. .......................... 435/6; 435/7.1; 435/69.1; 530/350
(58) Field of Search .......................... 435/6, 7.1, 69.1; 530/350

(56) References Cited

U.S. PATENT DOCUMENTS

| | | | |
|---|---|---|---|
| 5,681,824 A | 10/1997 | Christ et al. | |
| 2002/0019521 A1 | 2/2002 | Orr et al. | |
| 2002/0042379 A1 | 4/2002 | Rossignol et al. | |
| 2002/0183399 A1 | 12/2002 | Kang et al. | |

FOREIGN PATENT DOCUMENTS

| | | |
|---|---|---|
| WO | WO 00/77204 | 12/2000 |
| WO | WO 01/55386 | 8/2001 |

OTHER PUBLICATIONS

Smirnova et al, "Phylogenetic variation and polymorphism at the Toll–like receptor 4 locus (TLR4)", Genome Biology 1(1):1–10 (2000).
Xu et al, "Toll–Like Receptor–4 Is Expressed by Macrophages in Murine and Human Lipid–Rich Atherosclerotic Plaques and Upregulated by Oxidized LDL", Circulation 104:3103–3108 (2001).
Equils et al, "Bacterial Lipopolysaccharide Activates HIV Long Terminal Repeat Through Toll–Like Receptor 4", The Journal of Immunology 166:2342–2347 (2001).
Franchin et al, "Lipopolysaccharide Inhibits HIV–1 Infection of Monocyte–Derived Macrophages Through Direct and Sustained Down–Regulated of CC Chemokine Receptor 5", The Journal of Immunology 164:2592–2601 (2000).
Kiechl et al, "Toll–Like Recerptor 4 Polymorphisms and Atherogenesis", N. Engl. J. Med. 347(3):185–192 (2002).

*Primary Examiner*—Janet Andres
(74) *Attorney, Agent, or Firm*—Nixon & Vanderhye P.C.

(57) ABSTRACT

The present invention relates, in general, to toll-like receptor 4 (TLR4) mutations and, in particular, to a method of assessing the susceptibility of an individual to atherosclerosis and to a method of treating an individual identified as being at increased risk.

8 Claims, 2 Drawing Sheets

TOLL-LIKE RECEPTOR 4 MUTATIONS

The present application claims priority from U.S. Provisional Application No. 60/338,680, filed Dec. 11, 2001, the entire content of that application being incorporated herein by reference.

TECHNICAL FIELD

The present invention relates, in general, to toll-like receptor 4 (TLR4) mutations and, in particular, to a method of assessing the susceptibility of an individual to atherosclerosis and to a method of treating an individual identified as being at increased risk.

BACKGROUND

Endotoxin or lipopolysaccharide (LPS), released from the cell wall of bacteria, plays a central role in a broad spectrum of human disease. The pathogenic importance of LPS in gram-negative sepsis is well established. Intravenous LPS induces all of the clinical features of gram-negative sepsis, including fever, shock, leukopenia followed by leukocytosis, and disseminated intravascular coagulation (Favorite et al., J. Clin. Invest. 21:589 (1942)). Higher concentrations of circulating levels of endotoxin have been associated with manifestations of systemic inflammatory response syndrome (Wang et al., Clin. Nucl. Med. 20:494 (1995)) and the development of acute respiratory distress syndrome following sepsis (Brigham et al., Am. Rev. Respir. Dis. 133:913 (1986)).

The ability of the host to respond to endotoxin may play an important role in determining the severity of the physiologic and biologic response to this frequently encountered toxin. In mice, genetic differences in susceptibility to LPS have been established. Several reports suggest that humans may also respond differently to LPS. LPS is thought to cause much of its morbidity and mortality by activating kinases (DeFranco et al, J. Steroid Biochem. Mol. Biol. 65:51 (1998)) that control the function of transcription factors (nuclear factor-κB ans AP-1) and ultimately lead to production of pro-inflammatory cytokines and co-stimulatory molecules (Wright et al, J. Exp. Med. 189:605 (1999)). Several lines of evidence suggest that the toll receptor (TLR) family, specifically TLR4 and TLR2, regulate the interaction between LPS and intracellular kinases and may serve as a proximal target to interrupt LPS signaling (Wright et al, J. Exp. Med. 189:605 (1999), Medzhitov et al, Nature 388:394 (1997)). Both TLR4 and TLR2 activate signaling through NP-κB and AP-1 in transfected human cell lines (Medzhitov et al, Nature 388:394 (1997), Yang et al, Nature 395:284 (1998)), TLR4 mediates LPS induced signal transduction (Chow et al, J. Biol. Chem. 274:10689 (1999)). CD14, a glycosylphosylphosphatidyl inositol-linked receptor that binds LPS, enhances LPS induced TLR2 (Yang et al, Nature 395:284 (1998)) and TLR4 (Chow et al, J. Biol. Chem. 274:10689 (1999)) signaling, suggesting that the toll receptors interact with CD14 to initiate the cellular response to LPS. Studies in mice indicate that i) the TLR4 gene maps to the critical region in LPS hyporesponsive mice (Poltorak et al, Science 282:2085 (1998)), ii) mutations in the TLR4 gene (Poltorak et al, Science 282:2085 (1998); Qureshi et al., J. Exp. Med. 189:615 (1999)) are found in mouse strains (C3H/HeJ and C57BL10/ScCr) that are defective in their response to LPS, and iii) disruption of the TLR4 gene results in a LPS hyporesponsive phenotype (Hoshino et al, J. Immunol. 162:3749 (1999)). The human TLR4 gene has been shown to be polymorphic and a sequence polymorphism in the TLR4 gene has been shown to be associated with a hyporesponsive LPS phenotype in humans that interrupts LPS signaling (WO 00/77204). Recent characterization of common human TLR4 mutations demonstrates a highly variable efficacy of LPS signaling and capacity to elicit inflammation in humans (Arbour et al, Nat. Genet. 25:187 (2000)).

SUMMARY OF THE INVENTION

The present invention relates generally to TLR4 mutations. More specifically, the invention relates to a method of assessing the susceptibility of an individual to atherosclerosis and to a method of treating an individual identified as being at increased risk.

Objects and advantages of the present invention will be clear from the description that follows.

DETAILED DESCRIPTION OF THE INVENTION

Figure 1:
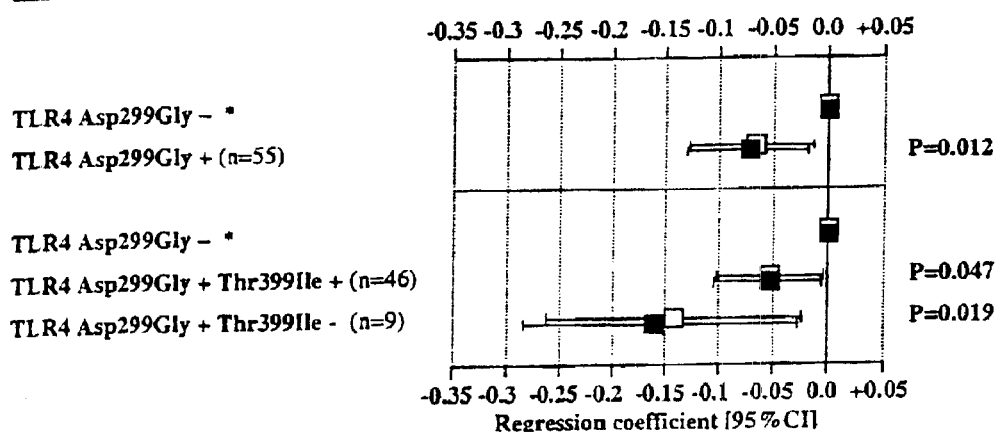
FIGS. 1A–1C: Association between common TLR4 mutations and measures of atherosclerosis severity and progression: Ors [95% CI] and regression coefficients [95% CI] were adjusted for age and sex (□)+LDL and HDL cholesterol, lipoprotein(a), hypertension, smoking status, alcohol consumption, ferritin, diabetes and microalbuminuria (■). Separate equations were fitted comparing Asp299Gly− vs. Asp299Gly+ or Asp299Gly− vs. Asp299Gly+/Thr399Ile+ vs. Asp299Gly+/Thr399Ile−. *reference group
Figure 1:
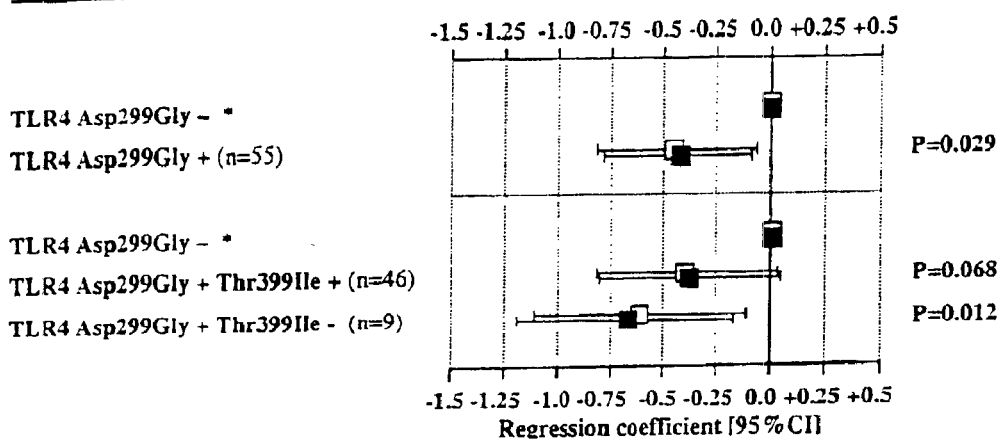
Figure 1:
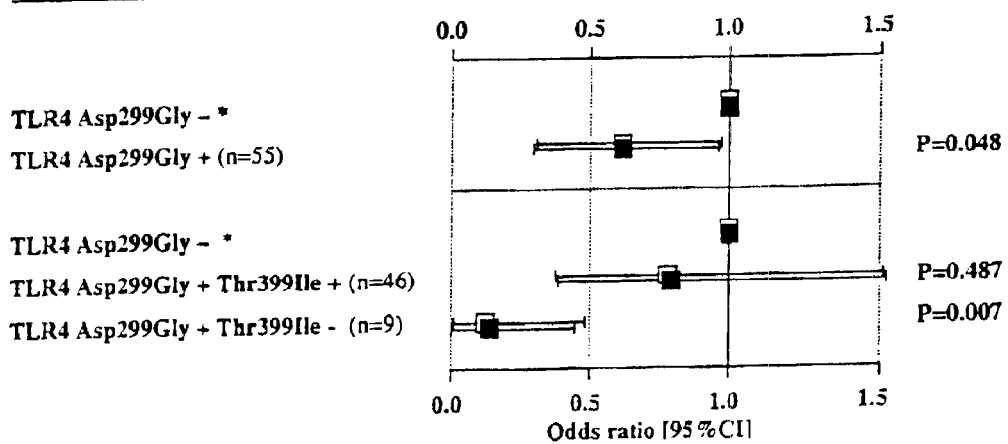

The present invention relates generally to a method of identifying a human at risk of, or having an indication associated with, altered innate immunity. More specifically, the invention relates to a method of identifying an individual at an increased (or decreased) risk of developing atherosclerosis. In a preferred embodiment, the present method comprises contacting an amount of DNA obtained from a human physiological sample with an amount of at least one TLR4-specific oligonucleotide under conditions effective to amplify the DNA so as to yield amplified DNA, and determining whether the amplified DNA encodes at least a portion of a variant TLR4. Where appropriate, the method can be carried out without amplification or alternative means of assessing the presence of a variant TLR4 can be used, such alternative methods being well known in the art (see, for example, WO 0000/77204).

The the present invention results from studies demonstrating that common TLR4 mutations that attenuate endotoxin signalling and diminish the host inflammatory response to inciting Gram negative pathogens are associated with a decreased atherosclerosis risk. More specifically, the results provided in Example 1 indicate that the Asp299Gly allele of TLR4, alone or, less pronounced, in combination with the Thr399Ile TLR4 allele, confers a low level of systemic inflammation and protects individuals from the development of atherosclerosis. These findings provide evidence for a role of endotoxin in atherogenesis and have several implications. First, the low levels of systemic inflammation observed in subjects with common TLR4 mutations correspond well with the in vitro impairment of endotoxin signaling and predict an increased susceptibility to severe acute bacterial infections as indicative of an attenuated innate immune defense. Available data indicate that the same allelic variants of TLR4 predispose people to develop septic shock with Gram negative miroorganisms. Second, part of the low-grade systemic inflammation measurable in healthy subjects appears to be mediated by the TLR4 pathway. The main ligand of TLR4 is LPS from common Gram negative bacteria including *C. pneumoniae* and *H. pylori*—the two pathogens most commonly implicated in human atherogenesis (Muhilestein et al, Circulation 97:633–636 (1998), Mayr et al, Circulation 102:833–839 (2000), Pasceri et al, Circulation 97:1675–1679 (1998), Markus et al, Circulation 100:832–837 (1999)). Recent evidence indicates that ligand specificity of TLR4 is less restricted than previously assumed (Takeuchi et al, Immunity 11:443–1451 (1999), Hou et al, Infect. Immun. 68:4681–4687 (2000)). Toxic lipoteichoic acid from gram-positive bacteria, for example, is also recognized by TLR4 and a functional cross-talk between the members of the TLR family has been proposed. Therefore, the innate inflammatory defense to a broad palette of bacterial and possibly viral microorganisms relies on an intact TLR4 pathway and part of these pathogens are commonly exposed to the immune system by minor translocations across the skin/mucosa barrier or within the course of infections. In addition, endogenous TLR4 ligands may exist. Human heat-shock protein 60 has been shown to be fully dependent on functional TLR4 regarding its stimulation of a TNFα and NO response (Ohashi et al, J. Immunol. 164:558–561 (2000)). Heat-shock protein 60 has been proposed to act as a danger antigen, which is over-expressed and partly released to circulation upon stimulation by various endo- and exogenous stress factors and by itself exerts pro-inflammatory effects, thus driving the (innate) defense system to increased alertness (Akira et al, Nat. Immunol. 2:675–680 (2001), Ohashi et al, J. Immunol. 558–561 (2000)). Third, the results provided herein demonstrate that a genetic variant rendering individuals susceptible to acute disseminated bacterial infection confers a decreased atherosclerosis risk. Vice versa, carriers of the wild-type allele capable of producing a prominent inflammatory response to virulent Gram negative pathogens can be predicted to be at higher risk of atherosclerosis in later life.

The invention is also useful in the development of drugs that target the TLR4 gene product, e.g., modulate the function of TLR4, especially the extracellular domain. These agents can thus be useful to prevent or ameliorate atherosclerosis. Agents suitable for use in the method of the invention can be identified using, for example, the screening protocols described in WO 00/77204. Examples of suitable agents include those disclosed in U.S. Pat. No. 5,681,824 and described by Christ et al, Science. 268(5207):80–3 (1995), Daun et al, J Endotoxin Res6(6):447–52 (2000) (e.g. E5564).

Certain aspects of the invention can be described in greater detail in the non-limiting Example that follows.

EXAMPLE 1

Experimental Details

Study subjects: The Bruneck Study is a prospective population-based survey of the epidemiology and etiology of atherosclerosis (Kiechl et al, Arterioscler. Throm. Vasc. Biol. 19:1484–1490 (1999), Kiechl et al, Arterioscler. Throm. Vasc. Biol. 19:1491–1498 (1999), NIH/CEPH Collaborative Mapping Group, Science 258:67–86 (1992)). At the 1990 baseline evaluation ($Q_0$), the study population was recruited as a sex- and age-stratified random sample of all inhabitants of Bruneck (125 women and 125 men in the 5th to 8th decades, each). A total of 93.6 percent participated, with data assessment completed in 919 subjects. Between 1990 and the reevaluations 1995 ($Q_1$) and 2000 ($Q_2$) subgroups of 63 and 106 individuals died or moved away. Among survivors follow-up was 96.5 percent ($Q_1$, n=826) and 94.0 percent ($Q_2$, n=701) complete. Blood specimens for DNA extraction were drawn as part of the 1995 follow-up. Thus, all main analyses focused on this evaluation.

Clinical history and examination: Hypertension was defined as blood pressure (mean of three measurements) $\geq 160/95$ or the use of antihypertensive drugs. Diabetes mellitus was coded present for subjects with fasting glucose levels $\geq 140$ mg/dL and/or a 2 hr value (oral glucose tolerance test) $\geq 200$ mg/dL.

Information on severe acute infections of bacterial origin including pneumonia, pyelonephritis, peritonitis, diverticulitis and sepsis were thoroughly collected over a 5-year period ($Q_1$ to $Q_2$) involving a detailed self-reported medical history, medical records provided by general practitioners, death certificates and reviews of the data bases of the Bruneck Hospital which is the only hospital in the whole district. Chronic infections were assessed by an extensive screening procedure as detailed previously (Kiechl et al, Circulation 103:1064–1070 (2001)).

Laboratory Methods: Blood samples were drawn after an overnight fast and 12 hours' abstinence from smoking (Willeit et al, Arteriosclerosis and Thrombosis 13:661–668 (1993)). In subjects with acute infection, blood drawing was delayed for at least $\geq 6$ weeks, i.e. until $\geq 4$–5 weeks after recovery from infectious illness. Markers of infection/inflammation were measured with commercial assays as follows: C-reactive protein, $\alpha_1$-antitrypsin and ceruloplasmin (nephelometry, Behring), soluble vascular-cell (sVCAM-1), soluble intracellular adhesion molecule 1 (sICAM-1), and E-selectin (enzyme-linked immunosorbent assay, R&D Systems and Bender), soluble interleukin-2 receptor (sIL-2r) (enzyme immunoassay, T cell Diagnostics), neopterin (radio-immunoassay, Henning), and interleukin-6 (IL-6) (enzyme amplified sensitivity immunoassay, Biosource).

DNA extraction and TLR4 genotyping: High-quality genomic DNA was prepared from frozen whole blood using the GENOMICPREP blood DNA isolation kit (Amersham Pharmacia Biotech, Uppsala, Sweden). Polymerase chain reaction (PCR) products were obtained from 810 of the 826 participants. Subsequent allele-specific PCR amplification for the TLR4 alleles Asp299Gly and Thr399Ile was performed according a previously described protocol (Lorenz et al, Biotchniques 31:22–24 (2001)). Genotypes were assigned blinded with respect to patient identity and phenotype.

In vitro study: To determine the ability of the various TLR4 alleles to signal in response to LPS, THP-1 cells were transfected with the various human TLR4 isoforms. THP-1 cells were passaged the day before the transfection to ensure healthy growth. On the day of the transfection, THP-1 cells were plated at a density of 5–7.5×10$^6$ in 60 mm$^2$ dishes in 4 ml of complete RPMI media. All transfection mixes included human MD-2 (gift of Dr. K Miyake, Saga Medical School), a necessary adapter molecule for TLR4-mediated LPS signaling. Transfections were done using the effectene kit (Qiagen) and were repeated a minimum of two times. 1 ml of total transfection mix was added to the cell suspension and incubated overnight. The next day, cells were stimulated with 100 ng/ml of LPS for 5 hours prior to lysis (Promega, Madison, Wis.). Cells were lysed in 1× lysis buffer (Promega, Madison, Wis.) overnight at 4° C. Protein contents of the lysates were measured using the BioRad protein assay reagent with 1.2 µl of lysate being added to 200 µl of diluted BioRad Protein reagent. The absorbance was read at 595 nm in a microplate reader from BioTek instruments (Scotts Valley, Calif.). Luciferase assays were done in triplicate using assay reagents purchased from Promega (Madison, Wis.). For each assay, 8 µl of lysate was added to 100 µl of luciferase assay reagent and read in a Luminometer Model Monolight 2010 (Analytical Luminescence Laboratories, San Diego, Calif.).

Assessment of atherosclerosis: The ultrasound protocol involves the scanning of the internal (bulbous and distal segments) and common carotid arteries (CCA) (proximal and distal segments) of either side with a 10-MHz imaging probe. Atherosclerotic lesions were defined according to two ultrasound criteria: (Kopp et al, Curr. Opin. Immunol. 11:13–18 (1999)) wall surface (protrusion or roughness of the arterial boundary) and (Akira et al, Nat. Immunol. 2:675–680 (2001)) wall texture (echogenicity). The maximum axial diameter of plaques was assessed in each of the eight vessel segments and an atherosclerosis score calculated as a global measure of atherosclerosis severity by addition of all diameters (intra-observer coefficient of variation, 13.5 percent (n=100)) (Willeit et al, Arteriosclerosis and Thrombosis 13:661–668 (1993)). In addition the development of new carotid plaques (incident atherosclerosis $Q_0$ to $Q_1$) was assessed in all subjects (kappa coefficients >0.8 (reproducibility sample n=100)) (Kiechl et al, Arterioscler. Throm. Vasc. Biol. 19:1484–1490 (1999), Kiechl et al, Arterioscler. Throm. Vasc. Biol. 19:1491–1498 (1999)). The intima-media thickness (IMT) was quantified at the far wall of plaque-free ("undiseased") sections of the CCAs as the distance between the lumen-intima and media-adventitia interface (intra-observer coefficient of variation, 7.9 percent (n=100)) (Kiechl et al, Arterioscler. Throm. Vasc. Biol. 19:1491–1498 (1999)).

Statistical analysis: Differences in the means of inflammation parameters in subjects with and without common TLR4 mutations were analyzed with the Student's t-test and analysis of variance. The association of TLR4 mutations with the presence and progression of carotid atherosclerosis was examined by logistic regression analysis (Hosmer et al, Applied Logistic Regression, New York, N.Y.: John Wiley & Sons Inc. (1988)). Multivariate equations were adjusted for a fixed set of covariates assessed in previous detailed analyses on vascular risk profiles in the Bruneck population (Willeit et al, Arterioscler. Thromb. Vasc. Biol. 20:529–537 (2000)). Logistic regression models were supplemented and confirmed by linear regression analysis employing the ln-transformed atherosclerosis score or the intima-media thickness as continuous outcome variables.

Results

Of the 810 men and women tested 53 were heterozygous for the TLR4 Asp299Gly allele and two were homozygous corresponding to an allelic frequency of 3.1 percent and carriage rate of 6.0 percent (rates standardized to the age/sex-structure of the general community in Bruneck). In a majority of these subjects co-segregation of the Thr399Ile mutation was observed (n=46, 25 men and 21 women). Among the remaining nine subjects with only the TLR4 Asp299Gly variant a clear male preponderance was evident (7 men and 2 women).

As compared with the wild-type carriers of the Asp299Gly allele tended to have lower levels of pro-inflammatory cytokines, acute-phase reactants, soluble adhesion molecules, and other components of the inflammation cascade. In men some of these trends reached a conventional level of statistical significance: IL-6 6.2 vs. 8.9 pg/mL, C-reactive protein 1.8 vs. 3.5 mg/L, procalcitonin 22.2 vs. 28.6 pg/mL, E-selectin 52 vs. 59 ng/mL, sICAM-1 320 vs. 350 ng/mL, sVCAM-1 563 vs. 684 ng/ML, sIL-2r 314 vs. 388 U/mL (P<0.05 each). Among carriers of the Asp299Gly allele, systemic inflammation tended to be lowest in those without co-segregation of the Thr399Ile allele and intermediate in subjects with coexistence of both mutations (Table 1). In contrast, no relations were observed between TLR4 genotypes and common vascular risk factor or life-style variable (blood pressure, lipids, smoking, body mass index, etc).

TABLE 1

Association between common toll-like receptor 4 mutations and levels of marker of inflammation in the Bruneck Study population (n = 810).

| Variable | Wild type TLR4 | TLR4 Asp299Gly and Thr399Ile | TLR4 Asp299Gly | P-value |
|---|---|---|---|---|
| Interleukin-6 - pg/mL | 9.6 | 6.7 | 4.7 | <0.05 |
| Procalcitonin - pg/mL | 31.9 | 26.8 | 20.3 | <0.05 |
| C-reactive protein - mg/L | 3.49 | 2.46 | 1.16 | 0.09 |
| $\alpha_1$-antitrypsin - mg/dL | 202 | 201 | 191 | 0.22 |
| Ceruloplasmin - mg/dL | 26.9 | 26.4 | 24.6 | 0.15 |
| Fibrinogen - mg/dL | 297 | 263 | 238 | <0.01 |
| Ferritin - ng/mL | 170 | 143 | 84 | 0.08 |
| sICAM-1 - ng/mL | 329 | 314 | 299 | 0.10 |
| sVCAM-1 - ng/mL | 726 | 584 | 526 | <0.05 |
| E-selectin - ng/mL | 54.1 | 50.6 | 47.5 | 0.22 |
| sIL-2r - U/ml | 330 | 251 | 250 | 0.11 |
| Neopterin - nmol/L | 8.3 | 7.6 | 6.1 | <0.01 |

Means presented were adjusted by age (58, 59 and 67 years in the various categories) and sex (50%, 54% and 78% males in the various categories). Factors to convert conventional units into SI units are as follows: $\alpha_1$-antitrypsin × 0.01 [g/L], ceruloplasmin × 10 [mg/L], fibrinogen × 0.01 [g/L], ferritin × 1 [µg/L].
sICAM-1, soluble intracellular adhesion molecules 1; sVCAM-1, soluble vascular-cell adhesion molecule 1.

Carriers of TLR4 mutations appear to be more susceptible to bacterial infections. In the current study population 53 subjects (6.4 percent) experienced severe acute infections of putative bacterial origin over a 5-year period. The frequency of prominent acute infectious illness was substantially higher among subjects with the Asp299Gly+/Thr399Ile− and Asp299Gly+/Thr399Ile+ genotypes (33 and 11 percent) than in those with TLR4 wild-type (6 percent) (P<0.001). In contrast, chronic infections occurred at similar rates in the various groups (45, 35 and 32 percent; P=NS).

Next, the potential effects of genetic variants of TLR4 on carotid artery disease were estimated thereby utilizing three distinct ultrasound measures of atherosclerosis severity and progression: CCA IMT—a frequently used surrogate of systemic vessel pathology, an atherosclerosis summing score (Willeit et al, Arteriosclerosis and Thrombosis 13:661–668 (1993)) and the person-based atherosclerosis progression model developed and validated within the Bruneck Study (Kiechl et al, Arterioscler. Throm. Vasc. Biol. 19:1484–1490 (1999), Kiechl et al, Arterioscler. Throm. Vasc. Biol. 19:1491–1498 (1999)). Results of these analyses are summarized in FIG. 1. In brief, whatever measure of atherosclerosis was applied, the TLR4 Asp299Gly allele emerged as a significant protective factor in the development of atherosclerosis. Beneficial effects were most pronounced in subjects without the commonly co-segregated Thr399Ile mutation (n=9). As to carriers of both genetic TLR4 variants (n=46) predictive significance was less consistent for the distinct atherosclerosis models (FIG. 1). Once focusing on the IMT and atherosclerosis score—the models with the highest mathematical power—inverse relations of moderate strength emerged which approached statistical significance.

Absolute differences in the measures of atherosclerosis (age/sex adjusted) were as follows: Asp299Gly+/Thr399Ile– and Asp299Gly+/Thr399Ile+ vs. Asp299Gly–: $\Delta$IMT –151 $\mu$m and –53 $\mu$m, $\Delta$ atherosclerosis score –3.11 mm and –0.86 mm.

All above results were virtually unchanged when adjusting the statistical models for common vascular risk factors (FIG. 1: adjusted odds ratios and regression coefficients are in black). The inverse association between the Asp299Gly TLR4 mutation and atherosclerosis risk tended to be stronger among men, which is explained by the clear male preponderance of the Asp299Gly+/Thr399Ile– genotype. However, there was no evidence of differential effects of TLR4 mutations in subgroups according to the levels of risk and life-style attributes.

Figure 2:
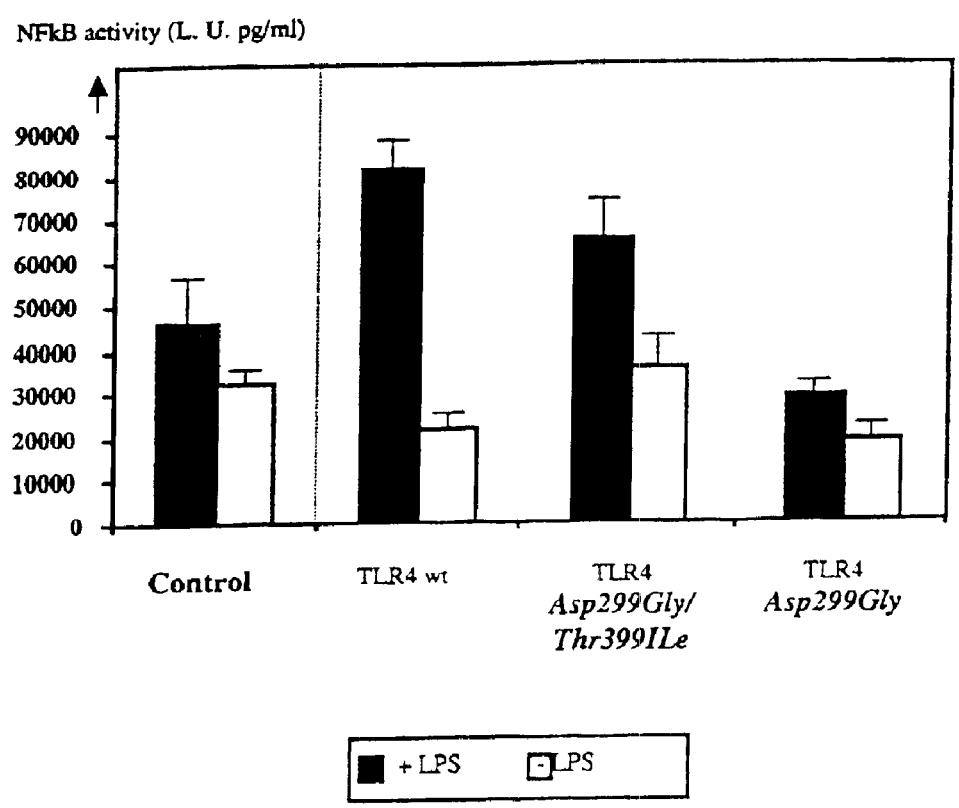
FIG. 2: Functional significance of TLR4 mutations in THP-1 cells: THP-1 cells were transfected with TLR4 expression plasmids (wild-type, Asp299Gly, Thr399Ile and Asp299Gly) and cells stimulated with LPS. NFκB activity following LPS stimulation (as measured by luciferase assay) was significantly less for THP-1 cells transfected with the Asp299Gly plasmid (P<0.01) or Asp299Gly and Thr399Ile plasmid (P=0.05) as compared with cells transfected with the wild-type TLR4 plasmid. All transfection were repeated at least twice. A mock transfection using the empty vector (pcDNA3.1+) was performed to correct for the background luciferase activity in THP-1 cells, which express TLR4, MD-2 and TLR2 endogenously. L.U., luciferase units.

The epidemiological findings were in close agreement with the results of in vitro experiments. In THP-1 cells transfected with expression plasmids of wild-type, Asp299Gly or Asp299Gly and Thr399Ile TLR4 impairment of signal transduction evoked by endotoxin binding was as follows (in descending order of priority): Asp299Gly>>Asp299Gly and Thr399Ile>wild-type (reference group) (FIG. 2) (Arbour et al, Nat. Genet. 25:187–191 (2000)).

All documents cited above are hereby incorporated in their entirety by reference.

What is claimed is:

1. A method of identifying a human at a decreased risk of developing atherosclerosis comprising obtaining a biological sample from said human and assaying said sample for the presence of a variant TLR4 that comprises an Asp299 Gly polymorphism, or a nucleic acid sequence encoding said variant, wherein the presence of said variant TLR4 is associated with a decreased atherosclerosis risk.

2. The method according to claim 1 wherein said sample is a nucleic acid sample.

3. The method according to claim 2 wherein said assay comprises: (a) contacting said nucleic acid with at least one TLR4-specific oligonucleotide under conditions effective to amplify said nucleic acid so as to yield amplified nucleic acid; and (b) determining whether said amplified nucleic acid encodes said variant TLR4.

4. The method according to claim 2 wherein said nucleic acid sample comprises genomic DNA.

5. The method of claim 2 wherein said nucleic acid sample comprises cDNA.

6. The method according to claim 1 wherein said sample is a protein sample.

7. The method according to claim 6 wherein said assay comprises contacting said sample with an antibody specific for said variant TLR4 and assaying for the presence of a complex comprising said antibody and said variant TLR4.

8. The method according to claim 1 wherein said variant TLR4 further comprises a Thr399Ile polymorphism.

* * * * *